United States Patent [19]

Roney

[11] Patent Number: 4,625,729

[45] Date of Patent: Dec. 2, 1986

[54] BODY COOLING CUFF

[76] Inventor: Lois Y. Roney, 604 Lookout Dr., Apt. 228, Richardson, Tex. 75080

[21] Appl. No.: 689,942

[22] Filed: Jan. 9, 1985

Related U.S. Application Data

[63] Continuation-in-part of Ser. No. 357,169, Mar. 11, 1982, abandoned.

[51] Int. Cl.[4] ............................................. A61F 7/10
[52] U.S. Cl. .................................... 128/402; 128/403
[58] Field of Search ............... 128/402, 403; 62/259.3, 62/530

[56] References Cited

U.S. PATENT DOCUMENTS

| | | | |
|---|---|---|---|
| 2,544,381 | 3/1951 | Goldmerstein | 128/402 X |
| 3,889,684 | 6/1975 | Lebold | 128/402 |
| 3,893,834 | 7/1975 | Armstrong | 128/403 X |
| 3,950,789 | 4/1976 | Konz et al. | 128/402 X |
| 3,951,127 | 4/1976 | Watson et al. | 128/403 X |
| 4,055,188 | 10/1977 | Pelton | 128/403 X |
| 4,204,543 | 5/1980 | Henderson | 128/402 |
| 4,381,025 | 4/1983 | Schooley | 128/402 X |
| 4,397,315 | 8/1983 | Patel | 128/403 |
| 4,488,552 | 12/1984 | McCann et al. | 128/402 |

*Primary Examiner*—Anton O. Oechsle
*Attorney, Agent, or Firm*—Vinson & Elkins

[57] ABSTRACT

A cuff-like device to provide personal cooling for the wearer, consisting of a flexible sealed envelope filled with a cold-retaining gel substance enclosed within an inner condensation-controlling and insulating fabric case which is enclosed within an outer case made of substantially impermeable material. The cuff-like device is fastened around the wrist by means of an adjustable insulated band.

1 Claim, 4 Drawing Figures

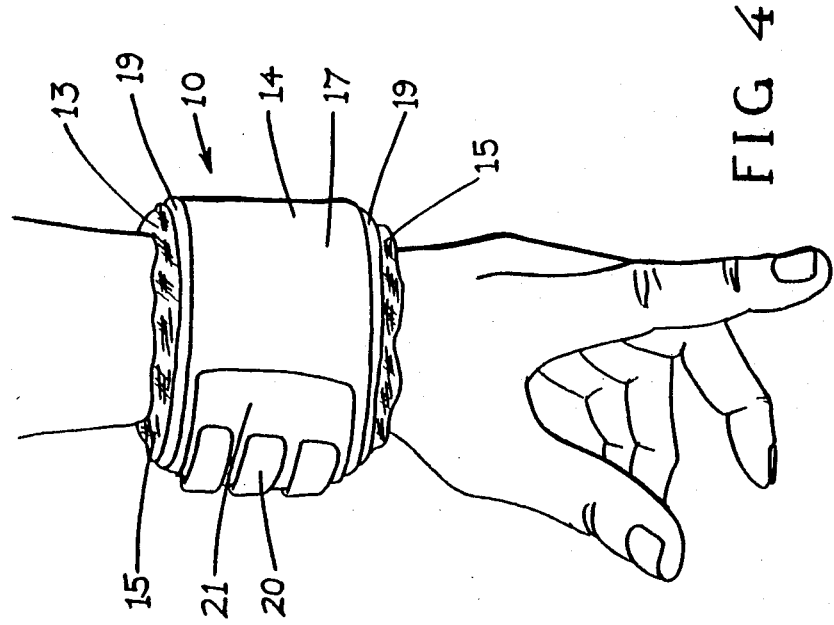
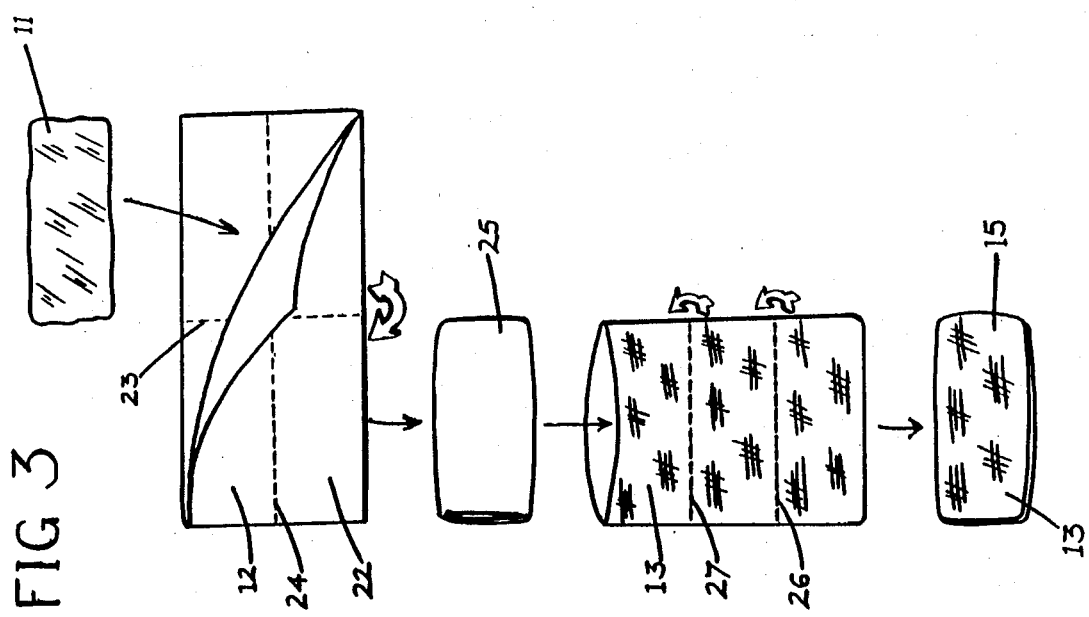

BODY COOLING CUFF

BACKGROUND

This application is a continuation-in-part of application Ser. No. 06/357,169 filed Mar. 11, 1982, abandoned.

This invention relates to a personal body-cooling device for use during hot or humid weather or in overheated indoor or outdoor working environments, and specifically to a cuff-like device consisting of a flexiible sealed inner envelope filled with a cold-retaining substance enclosed in an inner insulating and condensation-controlling layered fabric casing, which casing is in turn enclosed in an outer case made of substantially impermeable material. The device by means of an adjustable band is fastened around the wrist so as to capitalize on the specific neurophysiology of the lower hand and wrist.

Since it is not possible to cool the outdoors, and often not economical or not practical to cool an indoor environment, an inexpensive, light-weight, aesthetically acceptable, easy to assemble, comfortable to wear, and reasonably effective personal cooling device would fill a real need of a great many people: outdoors it would make life easier in the summertime for construction workers, oil field workers, farm workers, letter carriers, and so on, as well as gardeners, bicyclists, and people who just want or need to be out in spite of the heat. Indoors it would be helpful wherever air conditioing is need but not practical or not available.

Cooling devices for purposes of heat transfer between some particular portion of the human body and some cold-storing substance are well-known, but up to this time, the majority of these devices have uses which are simply therapeutic, intended to reduce pain, bleeding, and/or swelling in some localized area of the body. Examples of these devices are U.S. Pat. No. 4,055,188 Pelton, Therapeutic Wrap and U.S. Pat. No. 4,397,315 Patel, Dressing with Temperature Pack.

In addition to cooling devices which serve therapeutic purposes, there are cooling devices which are for cooling a body. Examples of these devices are U.S. Pat. No. 4,204,534, Henderson, Coolant Band; U.S. Pat. No. 3,950,789, Konz et al, Dry Ice Cooling Jacket; and U.S. Pat. No. 2,544,381, Goldmerstein, Cooling Belt, which are devices intended to cool the body as a whole. U.S. Pat. No. 4,204,543 consists of a perspiration-absorbing band to be worn about the head or wrists or inside a hat, the band containing small linked squares filled with a cold-retaining substance. U.S. Pat. No. 3,950,789 works by convection; it functions by establishing an area of cold carbon dioxide gas around the bare torso, holding it there by means of a nonporous jacket tightly fitted at the waist. U.S. Pat. No. 2,544,381 works by evaporation of water applied manually to a wide fabric belt worn about the waist, excess moisture being caught in a trough along the lower edge.

In addition to the devices that are intended to cool the body, there is U.S. Pat. No. 3,893,834, Armstrong, Insulated Cold Pack, which is intended to cool objects such as hyperdermic needles.

SUMMARY

The present invention is directed to a body cooling device for attachment to the wrist comprising a cold pack, an inner cloth case, an outer case, and means for attaching the outer case to the wrist. In the preferred embodiment, the cold pack contains a gel material and can be reused. The cloth case is made of absorbent washable material and has one end of one side closed. The cold pack is inserted in the cloth case, and the cloth case is folded over the cold pack thereby forming a plurality of layers. The outer case contains the cloth case and is made of material which is substantially impermeable to fluid.

The combination of the reuseable cold pack enclosed by the folded inner case forming a plurality of layers which is enclosed in the substantially impermeable outer case results in an efficient reuseable device for cooling the body while at the same time minimizing condensation problems which are inherent in all cooling devices. As moisture condenses, it is caught and absorbed by the fabric layer, but then as the whole packet warms up, the moisture evaporates in the air caught inside the packet. The result is that little if any moisture condenses on the outside of the cuff to interfere with the wearer's movement or to leak on his or her clothing.

The present invention also capitalizes on the specific neurophysiology of the hand and wrist. Not counting the cerebral cortex, in terms of sheer quantity of nerve endings, the hand and wrist area is the most complicated in the human body, followed closely by the mouth and speech area. These two areas together contain about two-thirds of the nerve endings in the body (R. Granit, *The Purposive Brain*, Cambridge, Mass.: M.I.T. Press, 1977, esp. pp. 64–65). Apparently for this reason, cold applied to the lower hand and wrist, as by the present invention, is both more comfortable (after an adjustment period of about 2 minutes) and more efficient in terms of drawing off excess body heat, than cold applied elsewhere to the body.

Moreover, the present invention further extends the effective cooling period by providing additional foam insulation on the inside of the cuff band.

In addition, the present invention is very easy to assemble, since the foldover fabric case and the outer case, even as they provide the layering of material and air necessary to cope with condensation, also eliminate any need for intricate threading or precision inserting of parts.

Furthermore, the present invention is both aesthetically acceptable and comfortable to wear, since, worn on the wrist, it does not add to the perceived bulk of the wearer's body and does not hamper the wearer's movements.

Still further, it is sufficiently effective, in spite of its simplicity, to keep its wearer reasonably comfortable in very high temperatures for periods ranging from 25 to 50 minutes depending on heat, humidity, and sunshine angle, at the end of which the wearer can, as soon as needed or desired, simply replace the warmed-up cold-retention unit with a fresh one and start the process over again.

And finally, the whole process is extremely efficient in terms of energy and ecology. Since home refrigerators run 24 hours a day anyway, the cold-retaining units are simply returned to the freezer to be refrozen and re-used again and again, so the whole process costs almost nothing. At outdoor work sites, picnic coolers filled with ice cool the units almost as efficiently.

BRIEF DESCRIPTION OF THE DRAWING

FIG. 3 illustrates assembly of the components (cold pack, foldover cloth case, and foldover plastic bag) prior to placement on the cuff-holder as in FIG. 1.

FIG. 4 shows the assembled body cooling cuff in use.

DETAILED DESCRIPTION OF THE EMBODIMENT

Figure 2:
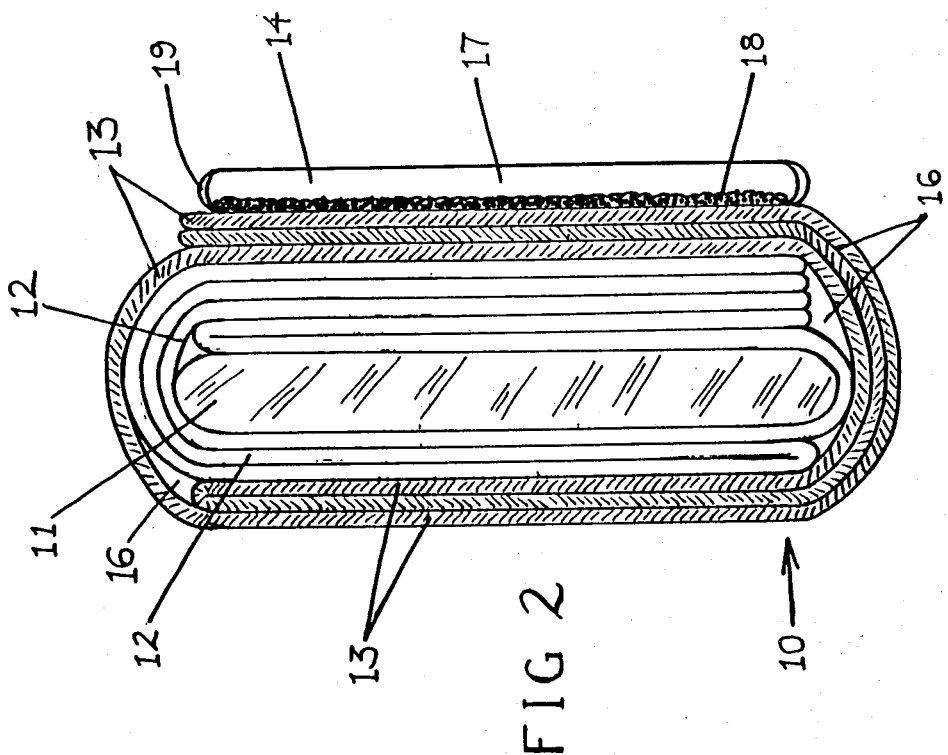
FIG. 2 shows a cross section through the middle of the body cooling cuff, revealing the central cold pack, the foldover layering of the inner cloth case and outer plastic bag, and the interstices for trapped air.
Figure 1:
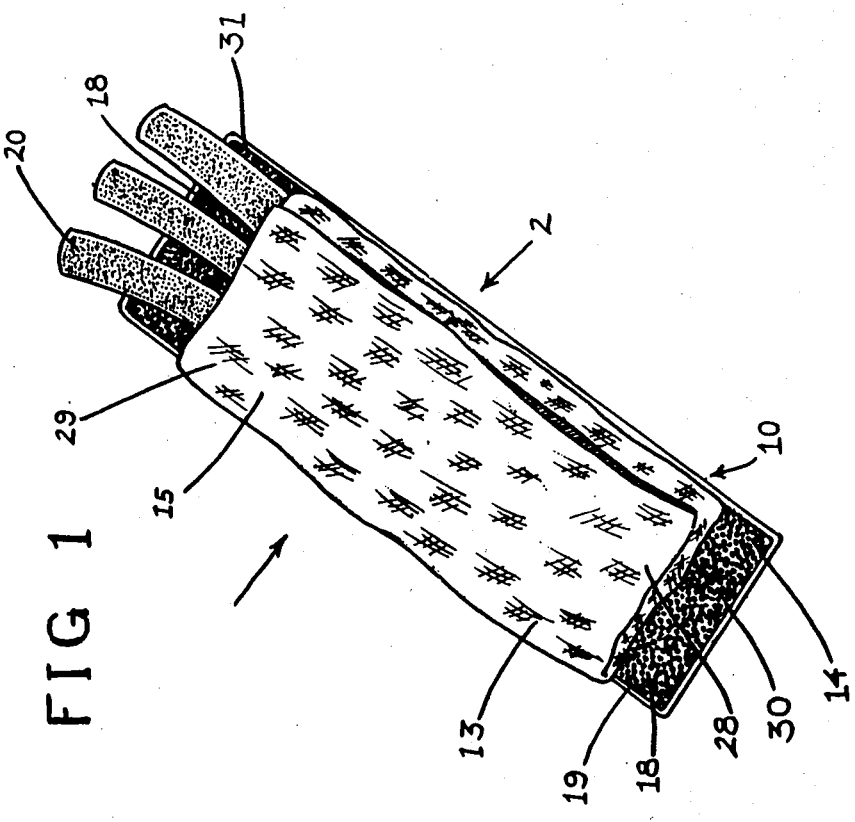
FIG. 1 shows the body cooling cuff assembled, ready to be fastened around the user's wrist.

Referring to FIGS. 1-4, there is shown a body cooling cuff generally designated 10 comprising a central re-usable cold pack 11, an inner foldover case 12 enclosing the central cold pack 11, an outer foldover case 13 enclosing the inner case 12 (itself enclosing the cold pack 11), and a cuff 14 for fastening the entire packet 15 (i.e., 13 enclosing 12 enclosing 11) around the wrist.

The central cold pack 11 consists of a re-usable permanently-sealed flexible plastic envelope containing refrigerant gel material.

As shown in FIG. 3, the inner foldover case 12 consists of two rectangularly-shaped layers of washable moderately-absorbent fabric (such as Permapress cotton percale) closed on one side and one end and open on one side and one end. As can be seen from the Figure, the length of a side of the inner case is approximately twice as long as the length of the cold pack 11, and the width of the inner case 12 is also approximately twice as long as the width of cold pack 11.

The outer foldover case 13 is made of a thin nonclinging waterproof plastic material, sufficiently stiff that when it is folded around the inner case 12 containing the cold pack 11, small pockets of air 16 will be trapped randomly here and ther in its own creases and layers and between it and the inner case 12. As can be seen in FIG. 3, the length of outer case 13 is approximately three times the corresponding dimension of the assembled package 25.

The cuff holder 14 is made of some sturdy fabric (such as heavy cotton, denim, or leather) on the outside 17, and is lined with foam insulation 18 on the inside, the two surfaces 17 and 18 of the cuff holder 14 being secured together with binding 19 around the edges. Velcro tabs 20 and square 21 are used to fasten the assembled body cooling cuff 10 around the wrist of the wearer FIG. 4. The use of the velcro tabs 20 and square 21 allows the user to adjust the device to the size of the user's wrist.

To assemble for each use (see FIG. 3), chilled central cold pack 11 is inserted into the inside corner 22 of inner case 12. Inner case 12 is then folded over twice, first on foldline 23 from right to left, and then on foldline 24 from front to back, thus forming insulated cold package 25 (which will have three layers of fabric on one side, five layers on the other). This package 25 is then inserted into the bottom of outer case 13 which is now folded over on foldlines 26 and 27 (resulting in three layers of plastic on each side) producing the entire packet 15. The layers formed by the folding of the outer case result in the trapping of air which aids in controlling condensation. The assembled packet 15 is now laid on the insulated side 18 of the cuff-holder 14 as in FIG. 1.

To use (see FIG. 4), the wearer lays one arm at right angles across the body cooling cuff 10, positioned palm or thumb side up and wrist completely within the cold packet 15, an then pulls the two ends 28 and 29 (See FIG. 1) of the cold packet 15 tightly together over the wrist, overlapping one over the other if possible. Then, holding the two ends 28 and 29 of the cold packet 15 down with the thumb, the wearer uses the fingers of the same hand first to pull the velcro-squared end 30 of the cuff holder 14 up over the two ends of the cold packet 15, and second to pull the end 31 of the cuff velcro-tabbed holder 14 up over the velcro square 21 and secure velcro tabs 20 to the velcro square 21. The entire assembly, from freezer to use, takes about 25 seconds.

To re-use, the wearer removes and disassembles the body cooling cuff 10, replaces the warmed central cold pack 11 with a chilled one, reassembles the body cooling cuff 10 and attaches it to the wrist again.

Although the preferred embodiment of this invention has been shown and described, it is understood that changes, modifications, variations, and substitutions may be made by someone with ordinary skill in the art without departing from the spirit and scope of this invention.

I claim:

1. A body cooling device for attachment to the wrist comprising
    a flexible, reusable, permanently sealed cold pack containing cooling material;
    a reusable cloth case containing the cold pack, said cloth case of absorbent washable material with one end and one side being closed, said cloth case being larger in size than the cold pack so that the cloth case can be folded over the cold pack when the cold pack is placed within said cloth case thereby forming a plurality of layers of the absorbent washable material;
    a reusble outer case containing the assembled cloth case and cold pack, said outer case being of material substantially impermeable to fluid, said outer case being foldable over the assembled cloth case and cold pack thereby forming a plurality of layers of the material substantially impermeable to fluid whereby air is entrapped between the layers;
    a cuff holder having ends and made of sturdy, flexible material, said cuff holder being lined with insulation on one side; and
    fastening means for fastening together the ends of the cuff holder when the cuff holder and the assembled outer case, cloth case and cold pack are placed around the wrist.

* * * * *